US005502087A

United States Patent [19]

Tateosian et al.

[11] Patent Number: 5,502,087
[45] Date of Patent: Mar. 26, 1996

[54] DENTAL COMPOSITION, PROSTHESIS, AND METHOD FOR MAKING DENTAL PROSTHESIS

[75] Inventors: Louis H. Tateosian, York; Scott E. Shaffer, Jacobus; Mark A. Latta, York, all of Pa.

[73] Assignee: Dentsply Research & Development Corp., Milford, Del.

[21] Appl. No.: 240,857

[22] Filed: May 16, 1994

Related U.S. Application Data

[63] Continuation-in-part of Ser. No. 81,940, Jun. 23, 1993, abandoned.

[51] Int. Cl.$^6$ .......................... A61C 13/08; A61C 13/00; C08F 120/18; C08F 120/20
[52] U.S. Cl. ........................ 523/115; 523/116; 433/168.1; 433/171; 433/199.1; 433/201.1; 433/213; 526/321; 526/323.1
[58] Field of Search ........................ 523/115, 116, 523/120; 433/168.1, 171, 199.1, 201.1, 213; 526/321, 323.1, 323.2

[56] References Cited

U.S. PATENT DOCUMENTS

| | | | |
|---|---|---|---|
| 68,548 | 9/1867 | Bean | 106/38.3 |
| 283,487 | 8/1883 | House | 425/180 |
| 1,575,688 | 3/1926 | Joannides | 425/180 |
| 2,341,991 | 2/1944 | Jackson | 425/180 |
| 2,660,758 | 12/1953 | Hennicke | 425/178 |
| 3,427,274 | 2/1969 | Cornell | 523/113 |
| 3,435,012 | 3/1969 | Nordlander | 523/176 |
| 3,470,615 | 10/1969 | Petner | 523/115 |
| 3,471,596 | 10/1969 | Petner et al. | 523/179 |
| 3,635,630 | 1/1972 | Greene | 425/175 |
| 3,647,498 | 3/1972 | Dougherty | 433/218 |
| 3,661,876 | 5/1972 | Wegemand et al. | 523/176 |
| 3,808,687 | 5/1974 | Millet | 433/213 |
| 3,889,385 | 6/1975 | Dougherty | 523/120 |
| 3,899,382 | 8/1975 | Matsuda et al. | 33/514 |
| 3,969,433 | 7/1976 | Kose et al. | 525/292 |
| 4,069,000 | 1/1978 | Hampshire | 425/395 |
| 4,081,492 | 3/1978 | Traenckner et al. | 525/531 |
| 4,092,303 | 5/1978 | Behrens | 525/244 |

(List continued on next page.)

FOREIGN PATENT DOCUMENTS

| | | |
|---|---|---|
| 1102039 | 5/1981 | Canada . |
| 1145880 | 5/1983 | Canada . |
| 1148294 | 6/1983 | Canada . |
| 1149538 | 7/1983 | Canada . |
| 1189996 | 7/1985 | Canada . |
| 1200046 | 1/1986 | Canada . |
| 1209298 | 8/1986 | Canada . |
| 1243796 | 10/1988 | Canada . |
| 1245437 | 11/1988 | Canada . |
| 1244581 | 11/1988 | Canada . |
| 1244177 | 11/1988 | Canada . |
| 1259149 | 9/1989 | Canada . |
| 1262791 | 11/1989 | Canada . |
| 2002017 | 5/1990 | Canada . |
| 2009471 | 8/1990 | Canada . |
| 2032773 | 6/1991 | Canada . |
| 2033405 | 7/1991 | Canada . |
| 2051333 | 9/1991 | Canada . |
| 0059525 | 9/1982 | European Pat. Off. . |
| 0185431A3 | 6/1986 | European Pat. Off. . |
| 0089705 | 12/1986 | European Pat. Off. . |
| 0334256A2 | 9/1989 | European Pat. Off. . |
| 0346707 | 12/1989 | European Pat. Off. . |
| 0193514 | 8/1990 | European Pat. Off. . |
| 0427300 | 5/1991 | European Pat. Off. . |
| 1516455 | 9/1969 | Germany . |
| 3236835A1 | 4/1984 | Germany . |
| 3725502 | 2/1988 | Germany . |
| 4102129A1 | 7/1992 | Germany . |
| 60-214284 | 10/1985 | Japan . |
| 62-54739 | 3/1987 | Japan . |
| 2189793 | 4/1987 | United Kingdom . |
| 87/05800 | of 0000 | WIPO . |

OTHER PUBLICATIONS

Lexatemp–Automix—Jan. 1992.
DMG Hamburg—Jan. 1992.
Dental Laboratory Procedures, vol. One 1986, pp. 276–311.
Radiation Curing, May 1984, pp. 4, 6, 8, and 9 and Radiation Curing, Aug. 1986.
Product Bulletin, 12 pages.
Rubber and Plastic Research Abstracts, 6 pages.
Oligomer Product Guide, 3 pages.
Sartome Company, 4 pages.
Product Catalog, pp. 18–21.
Advanced Plasma Systems, Inc., 4 pages.
Technique Manual and Operation/Service Manuel in Triad® VLC System, 3 pages.
Flexure Fatigue of Denture Bases, Journal of Denture Research, 1988, International Association for Dental Research.
The Journal of American Dental Association, vol. 28, pp. 489–504.

*Primary Examiner*—Peter A. Szekely
*Attorney, Agent, or Firm*—Dale R. Lovercheck; James B. Bieber; Edward J. Hanson, Jr.

[57] ABSTRACT

A dental prosthesis includes polymeric material formed by heat curing a polymerizable composition having at least 5 percent by weight of at least one polymerizable Monomer having at least one acrylic moiety and a gram molecular weight of at least 200. The polymeric material is preferably formed by heat curing and has an unnotched Izod impact strength of at least 2.5 and more preferably at least 3.0 ft.lb/in as measured by a Modified ASTM D256, and a flexural fatigue life of at least 20,000 flexes to failure at 0.1 inch deflection. Preferably the polymerizable monomer has a vapor pressure less than 5 mm Hg at 23° C. A method of making a denture is provided which includes molding and polymerizing the polymerizable composition to form a denture. Preferably the polymerizable composition includes polymerizable compounds made up of at least 5 percent by weight of the acrylic Monomer having a gram molecular weight of at least 300 and less than 5 percent by weight of Volatile compounds and less than 2 percent by weight of Low Molecular Weight acrylic compounds having a gram molecular weight of less than 200.

46 Claims, No Drawings

U.S. PATENT DOCUMENTS

| | | | |
|---|---|---|---|
| 4,097,994 | 7/1978 | Reaville et al. | 523/115 |
| 4,104,333 | 8/1978 | Lee, Jr. et al. | 523/113 |
| 4,115,922 | 9/1978 | Alderman | 433/26 |
| 4,129,611 | 12/1978 | Heiss | 525/440 |
| 4,155,890 | 5/1979 | Hofacker-Freifrau Von Nostitz | 523/115 |
| 4,182,507 | 1/1980 | Bekey et al. | 425/2 |
| 4,218,205 | 8/1980 | Beu | 425/180 |
| 4,229,431 | 10/1980 | Lee, Jr. et al. | 424/61 |
| 4,267,133 | 5/1981 | Kohmura et al. | 433/168.1 |
| 4,330,283 | 5/1982 | Michl et al. | 523/115 |
| 4,331,580 | 5/1982 | Bunyan | 523/176 |
| 4,359,435 | 11/1982 | Kogure | 425/812 |
| 4,394,465 | 7/1983 | Podszun et al. | 523/116 |
| 4,396,377 | 8/1983 | Roemer et al. | 523/115 |
| 4,396,476 | 8/1983 | Roemer et al. | 523/115 |
| 4,396,477 | 8/1983 | Jain | 204/182.1 |
| 4,426,504 | 1/1984 | Nandi | 523/115 |
| 4,427,809 | 1/1984 | Alberts et al. | 524/37 |
| 4,431,421 | 2/1984 | Kawahara et al. | 523/115 |
| 4,431,787 | 2/1984 | Werber | 523/176 |
| 4,433,077 | 2/1984 | Callander | 523/344 |
| 4,454,258 | 6/1984 | Kawahara et al. | 523/116 |
| 4,533,325 | 8/1985 | Blair et al. | 433/171 |
| 4,540,723 | 9/1985 | Ying | 523/115 |
| 4,543,395 | 9/1985 | Mancinelli | 525/332.4 |
| 4,544,711 | 10/1985 | Mancinelli | 525/332.3 |
| 4,551,098 | 11/1985 | Blair | 433/171 |
| 4,551,388 | 11/1985 | Schlademan | 428/355 |
| 4,551,486 | 11/1985 | Tateosian et al. | 523/115 |
| 4,563,153 | 1/1986 | Schaefer | 433/223 |
| 4,567,239 | 1/1986 | Mancinelli | 525/309 |
| 4,587,330 | 5/1986 | Warfel et al. | 528/490 |
| 4,599,216 | 7/1986 | Rohrer et al. | 422/21 |
| 4,602,076 | 7/1986 | Ratcliffe et al. | 526/301 |
| 4,609,351 | 9/1986 | Blair | 433/55 |
| 4,618,703 | 10/1986 | Thanawalla et al. | 525/532 |
| 4,636,540 | 1/1987 | Warfel | 523/310 |
| 4,650,550 | 3/1987 | Milnes et al. | 423/202.1 |
| 4,656,213 | 4/1987 | Schlademan | 524/272 |
| 4,657,941 | 4/1987 | Blackwell et al. | 523/116 |
| 4,674,980 | 6/1987 | Ibsen et al. | 523/115 |
| 4,688,801 | 8/1987 | Reiter | 273/235 R |
| 4,689,015 | 8/1987 | Denyer et al. | 524/115 |
| 4,698,373 | 10/1987 | Tateosian et al. | 523/115 |
| 4,704,303 | 11/1987 | Cornell | 424/61 |
| 4,705,476 | 11/1987 | Blair | 433/171 |
| 4,711,913 | 12/1987 | Tateosian et al. | 523/115 |
| 4,722,947 | 2/1988 | Thanawalla et al. | 525/303 |
| 4,722,976 | 2/1988 | Ceska | 525/301 |
| 4,745,138 | 5/1988 | Thanawalla et al. | 525/307 |
| 4,771,112 | 9/1988 | Engelbrecht | 525/327.3 |
| 4,806,381 | 2/1989 | Engelbrecht et al. | 523/116 |
| 4,816,495 | 3/1989 | Blackwell et al. | 523/116 |
| 4,842,936 | 6/1989 | Kashihara et al. | 523/400 |
| 4,844,144 | 7/1989 | Murphy et al. | 522/79 |
| 4,857,571 | 8/1989 | Reiter et al. | 524/248 |
| 4,863,977 | 9/1989 | Tateosian et al. | 524/504 |
| 4,872,936 | 10/1989 | Engelbrecht | 523/116 |
| 4,873,269 | 10/1989 | Nakazato | 523/115 |
| 4,874,675 | 10/1989 | Ceska | 428/521 |
| 4,880,857 | 11/1989 | Mori et al. | 523/205 |
| 4,892,478 | 1/1990 | Tateosian et al. | 433/6 |
| 4,928,403 | 5/1990 | Nakamura | 36/34 A |
| 4,938,831 | 7/1990 | Wolf, Jr. | 522/14 |
| 4,940,749 | 7/1990 | Mori et al. | 523/205 |
| 4,971,735 | 11/1990 | Uebayashi | 264/17 |
| 4,994,520 | 2/1991 | Mori et al. | 524/547 |
| 5,037,473 | 8/1991 | Antonucci et al. | 523/118 |
| 5,063,255 | 11/1991 | Hasegawa et al. | 523/109 |
| 5,066,231 | 11/1991 | Oxman et al. | 433/214 |
| 5,091,441 | 2/1991 | Omura | 523/176 |
| 5,094,619 | 3/1992 | McLaughlin | 523/115 |
| 5,104,591 | 4/1992 | Masuhara et al. | 264/16 |
| 5,108,753 | 4/1992 | Kuberasampath et al. | 424/422 |
| 5,137,952 | 8/1992 | Miller et al. | 524/140 |
| 5,147,903 | 9/1992 | Podszun et al. | 523/115 |
| 5,151,279 | 9/1992 | Kimura | 425/178 |
| 5,158,717 | 10/1992 | Lai | 425/808 |
| 5,183,834 | 2/1993 | Gorlich et al. | 523/115 |
| 5,210,109 | 5/1993 | Tateosian et al. | 523/115 |
| 5,218,070 | 6/1993 | Blackwell | 523/113 |

DENTAL COMPOSITION, PROSTHESIS, AND METHOD FOR MAKING DENTAL PROSTHESIS

This is a continuation-in-part of U.S. patent application Ser. No. 08/081,940 filed Jun. 23, 1993, now abandoned.

The invention relates to compositions and methods for making dental prostheses. The invention provides dental prostheses formed form one-component heat curable compositions without Volatile Monomers such as methyl methacrylate which form dental prostheses having high impact strength, and a method of making dental prostheses therefrom without the need for mixing i.e., a one-component system. Dental prostheses made in accordance with a preferred embodiment of the invention include polymeric material which is formed from a composition having at least 5 percent by weight of acrylic Monomers having at least one or more preferably at least two acrylic moieties having a gram molecular weight of at least 200 and more preferably at least 300, polymer particles which are readily reactive with, swollen by, or superficially dissolved by the acrylic Monomer and less than 10 percent by weight more preferably less than 5 percent by weight and most preferably less than 2 percent by weight Low Molecular Weight Monomer. Dental prostheses in accordance with the invention preferably having an unnotched Izod impact strength of at least 2.5 and more preferably at least 3.0 ft. lb/in measured by Modified ASTM D256, and at least 20,000 and more preferably at least 50,000 flexes to failure using the Flexural Fatigue of Denture Bases Test. Dental prostheses of the invention include denture base, artificial teeth, fillings, inlays, crowns and bridges.

Cornell in U.S. Pat. No. 3,427,274 disclose impact resistant alkali-washed mixed butadiene-styrene and methyl methacrylate molding composition. Birger in U.S. Pat. No. 3,435,012 discloses anaerobic sealant composition containing monoacrylate esters. Petner in U.S. Pat. No. 3,470,615 discloses dental crowns faced with polyglycol dimethacrylate and process for making. Petner in U.S. Pat. No. 3,471,596 discloses process of making fused thermosetting dental objects. Dougherty in U.S. Pat. No. 3,647,498 discloses process for production of dental crowns. Bernd et al in U.S. Pat. No. 3,661,876 disclose adhesives or sealing agents which harden on exclusion of oxygen. Millet in U.S. Pat. No. 3,808,687 discloses method of making dental restorations and pontic member therefor. Dougherty in U.S. Pat. No. 3,889,385 discloses liquid dental opaquer and method. Matsuda et al in U.S. Pat. No. 3,899,382 discloses anaerobic bonding agent. Kose et al in U.S. Pat. No. 3,969,433 disclose iridescent composition and the process of preparing the same. Behrens in U.S. Pat. No. 4,092,303 discloses polyacrylate elastomers with improved elasticity. Lee, Jr. et al in U.S. Pat. No. 4,104,333 disclose self-curing artificial fingernails. Alderman in U.S. Pat. No. 4,115,922 discloses dental crown and bridge shading system. Heiss in U.S. Pat. No. 4,129,611 discloses thermoplastic polyurethanes of mixtures of hard and soft thermoplastic polymers. Lee, Jr. et al in U.S. Pat. No. 4,229,431 discloses method of applying self-curing artificial nails. Kohmura et al in U.S. Pat. No. 4,267,133 disclose manufacture of denture base. Bunyan in U.S. Pat. No. 4,331,580 discloses flowable anaerobic sealant composition. Podszun et al in U.S. Pat. No. 4,394,465 disclose dental materials based on organic plastics in paste form. Roemer et al in U.S. Pat. No. 4,396,476 disclose blend of cross-linked polymer, swelling monomer and cross-linking agent and curing process. Roemer et al in U.S. Pat. No. 4,396,477 disclose dental appliances having interpenetrating polymer networks. Alberts et al in U.S. Pat. No. 4,427,809 disclose thermoplastic molding compositions of co-graft polymers. Werber in U.S. Pat. No. 4,431,787 discloses anaerobic adhesives. Callander in U.S. Pat. No. 4,433,077 discloses process for preparing curable compounds. Kawahara et al in U.S. Pat. No. 4,454,258 disclose resin-forming material, implant material and compositions for restorative material suitable for medical or dental use. Blair et al in U.S. Pat. No. 4,533,325 disclose method and apparatus to produce artificial teeth for dentures. Blair in U.S. Pat. No. 4,551,098 discloses method and apparatus to produce artificial teeth. Tateosian et al in U.S. Pat. No. 4,551,486 disclose interpenetrating polymer network compositions. Schaefer in U.S. Pat. No. 4,563,153 discloses dental composition containing pigment and methods of using the same. Ratcliffe et al in U.S. Pat. No. 4,602,076 disclose photopolymerizable compositions. Blair in U.S. Pat. No. 4,609,351 discloses apparatus to produce artificial dentures. Milnes et al in U.S. Pat. No. 4,650,550 discloses manufacture and repair of dental appliances. Blackwell et al in U.S. Pat. No. 4,657,941 disclose biologically compatible adhesive containing a phosphorus adhesion promoter and a sulfinic accelerator. Ibsen et al in U.S. Pat. No. 4,674,980 disclose dental composite and porcelain repair. Denyer et al in U.S. Pat. No. 4,689,015 disclose dental compositions. Tateosian in U.S. Pat. No. 4,698,373 discloses stable one part dental compositions employing IPN technology. Cornell in U.S. Pat. No. 4,704,303 discloses nail extension composition. Blair in U.S. Pat. No. 4,705,476 discloses method and apparatus to produce artificial dentures. Tateosian et al in U.S. Pat. No. 4,711,913 disclose interpenetrating polymer network compositions employing rubber-modified polymers. Engelbrecht in U.S. Pat. No. 4,771,112 discloses compounds that consist of aldehyde, epoxide isocyanate, or halotriazine groups of polymerizable groups, and of a higher-molecular backbone, mixtures that contain them, and the use thereof. Engelbrecht et al in U.S. Pat. No. 4,806,381 disclose polymerizable compounds containing acid and acid derivatives, mixtures containing the same, and use thereof. Blackwell et al in U.S. Pat. No. 4,816,495 disclose biologically compatible adhesive visible light curable compositions. Kashihara et al in U.S. Pat. No. 4,842,936 disclose composite basic resin particles, its preparation and resinous composition for coating use containing the same. Tateosian et al in U.S. Pat. No. 4,863,977 disclose process for preparing interpenetrating polymer network objects employing rubber-modified polymers. Engelbrecht in U.S. Pat. No. 4,872,936 discloses polymerizable cement mixtures. Mori et al in U.S. Pat. No. 4,880,857 disclose carbon black-graft polymer, method for production thereof, and use thereof. Tateosian in U.S. Pat. No. 4,892,478 discloses method of preparing dental appliances. Nakamura in U.S. Pat. No. 4,928,403 discloses plastic heels of shoes and boots. Wolf, Jr. in U.S. Pat. No. 4,938,831 discloses bonding method for preparing automotive headlamp assemblies. Mori et al in U.S. Pat. No. 4,940,749 disclose carbon black-graft polymer method for production thereof, and use thereof. Mori et al in U.S. Pat. No. 4,994,520 disclose carbon black-graft polymer, method for production thereof, and use thereof. Antonucci et al in U.S. Pat. No. 5,037,473 disclose denture liners. Omura in U.S. Pat. No. 5,091,441 discloses dental composition. Tateosian et al in U.S. Pat. No. 5,210,109 disclose interpenetrating polymer network compositions employing rubber-modified polymers. Blackwell in U.S. Pat. No. 5,218,070 discloses dental/medical compositions and use. Ying in Canadian Patent 1,259,149 discloses dental restorative composition containing monofunctional monomer. Howard et al in Canadian Patent 1,102,039 disclose radiation curable coating compositions containing unsaturated addition-polymerizable urethane resin. Suling et al in Canadian Patent 1,145,880 disclose molded dental pigments. Denyer et al in Canadian Patent 1,148,294 disclose dental compositions Ikeda et al in Canadian Patent 1,149,538 disclose curable resin compositions. Ratcliffe et al in Canadian Patent 1,189,996 disclose polymerizable dental composition containing a mixture of fine particle size and large particle size fillers. Fellmann et al in Canadian Patent 1,200,046 disclose permanent dental restorative material. Michael et al in Canadian Patent 1,209,298 discloses photopolymerizable composition especially for dental purposes. Ibsen et al discloses in Canadian Patent 1,243,796 dental composite and porcelain repair. Ibsen et al in Canadian Patent 1,244,177 discloses methacrylate functional resin dental composite and porcelain repair compositions. Schaefer in Canadian patent 1,244,581 discloses priming material for plastic dental members. Randklev in Canadian Patent 1,245,437 discloses radiopaque low visual opacity dental composites containing non-vitreous microparticles. Waknine in Canadian patent 1,262,791 discloses two component (Paste-Paste) self curing dental restorative material. Okada et al in Canadian Patent Application 2,002,017 disclose dental restorative material. Heid et al in Canadian Patent Application 2,009,471 discloses hybrid plastic filling material. Mitra et al in Canadian Patent Application 2,032,773 disclose dental compositions, a method of making shaped dental articles via photoiniferter polymerization of the dental compositions, and shaped dental articles produced thereby. Holmes in Canadian Patent Application 2,033,405 discloses dental material containing anti-slump additive. Rheinberger in Canadian Patent Application 2,051,333 discloses polymerizable dental material. Tateosian et al in European Patent Application 0 334 256 A2 disclose dental appliance preparation and material therefor. Muramoto et al in European Patent Application 0 185 431 A3 disclose composite resin particles, its preparation and resinous composition for coating use containing the same. Kuboto et al in U.K. Patent Application GB 2,189,793A disclose Polymerizable compositions for dental restoration. Heynold et al in PCT/DE87/00135 discloses polymerizable mass for production of non-hardening moulded elements, particular of dental prostheses. Luxatemp-Automix discloses a cartridge for polymerization. DMG HAMBURG discloses paste containing cannulas. Morrow et al disclose waxing and processing in Dental Laboratory Procedures, Volume One 1986, pages 276–311. Miller discloses acrylourethane resin design in Radiation Curing at pages 4, 6, 8, 9. Sartomer discloses urethane acrylate in Product Bulletin, 12 pages. Miller discloses monomers in Rubber & Plastics Research Abstracts, 6 pages. Sartomer discloses aliphatic and aromatic urethane acrylates in Oligomer Product Guide, 3 pages. Sartomer discloses in low skin irritation monomers in Sartomer Company, 4 pages. Sartomer discloses monomers, oligomers, and photoinitiators in Product Catalog, pages 18–21. Advanced Plasma Systems, Inc. discloses new D-series table-top gas plasma system, 4 pages. Dentsply discloses technique manual and operation/service manual in Triad® VLC System, 3 pages. Wilson et al, Flexure Fatigue of Denture Bases, Journal of Dental Research, 1988, International Association for Dental Research.

The prior art does not provide a dental prosthesis made of a polymeric material having an unnotched Izod impact strength of at least 3.0 as measured by Modified ASTM D256, and 20,000 flexes to failure using the Flexural Fatigue of Denture Bases Test, formed by heat curing a one-component polymerizable composition including at least 5 percent by weight of at least one polymerizable acrylic Monomer, having at least one and more preferably at least two acrylic moieties and a gram molecular weight of at least 200 and more preferably at least 300 as is provided by the present invention.

It is an object of the invention to provide a method of making a prosthesis by providing polymerizable composition including particulate polymer and at least 5 percent by weight of acrylic Monomers at least one and more preferably at least two acrylic moieties and a molecular weight greater than 200 and more preferably greater than 300 and a vapor pressure less than 5 mm at 23° C., molding and heat curing said polymerizable composition to form a prosthesis with an impact strength of at least 2.5 and more preferably at least 3.0 ft.lbs/in by a Modified ASTM D256 unnotched impact strength as hereinafter described and 20,000 flexes to failure using the Flexural Fatigue of Denture Bases Test.

It is an object of the invention to provide a denture base of a polymeric material having at least 20,000 flexes to failure using the Flexural Fatigue of Denture Bases Test formed by heat curing at least one polymerizable Monomer having at least one and more preferably at least two acrylic moieties and a gram molecular weight of greater than 200 and more preferably greater than at least 300.

Prosthesis as used herein refers to dental replacement parts and ancillary materials including dentures, fillings, crowns, bridges, teeth, and also dental restorative materials including filling and inlays.

"Volatile" as used herein refers the compounds having a vapor pressure greater than 5 mm Hg at 23° C., for example methyl methacrylate.

"Non-Volatile" as used herein refers the compounds having a vapor pressure less than 5 mm Hg at 23° C.

"Flexural Fatigue of Denture Bases Test" as used herein refers to the test described by Wilson, W. D., Tateosian, L. H., Grunden, C. J., Wagner, R. L., Flexural Fatigue of Denture Bases, J. Dent. Res. 67:196, 1988. The flexural fatigue of a denture base material is studied by subjecting a rectangular-shaped specimen to repeated bending on a four-way bending machine. The specimen is supported at both ends and the load is applied at the midpoint to bend the sample. The specimen is tested until failure by continuous cycling on the machine which bends the sample first in one direction, then in the opposite direction. This is called a four-way cycle; one cycle gives two flexes. The cycling speed is 100 cycles per minute (200 flexes per minute) which is reported to be approximately twice the chewing speed of a "normal" individual. The bend or deflection distance is set to 0.1 inch to exaggerate the movement which occurs when a denture is used in-the-mouth. A counter records each cycle and the machine stops when the specimen breaks. The number of cycles to failure is recorded for each specimen and the median number of flexes to break is calculated for each material. The material with the higher number of flex cycles until break is the more desirable material.

"Modified ASTM D256" as used herein refers to ASTM D256 conducted using unnotched samples which are 2.85× 11×85 mm.

"Low Molecular Weight" as used herein refers to gram molecular weight less than 200, for example, methyl methacrylate.

"Monomer(s)" as used herein refer to mono and polyfunctional monomers and/or oligomers.

"Diluent Monomers" as used herein refers to monomers having a viscosity of less than about 1000 cps measured at 23° C. measured by ASTM D2393-68 and gram molecular weights in the range of 200 to 600.

"Catalyst" as used herein includes free radical generating polymerization initiators.

SUMMARY OF THE INVENTION

A dental prosthesis includes polymeric material formed by heat curing a polymerizable composition having at least 5 percent by weight of at least one polymerizable Monomer having at least one acrylic moiety and a gram molecular weight of at least 200. The polymeric material is preferably formed by heat curing and has an unnotched Izod impact strength of at least 2.5 and more preferably at least 3.0 ft.lb/in as measured by a Modified ASTM D256, and a flexural fatigue life of at least 20,000 flexes to failure at 0.1 inch deflection. Preferably the polymerizable monomer has a vapor pressure less than 5 mm Hg at 23° C. A method of making a denture is provided which includes molding and polymerizing the polymerizable composition to form a denture. Preferably the polymerizable composition includes polymerizable compounds made up of at least 5 percent by weight of the acrylic Monomer having a gram molecular weight of at least 300 and less than 5 percent by weight of Volatile compounds and less than 10 percent by weight more preferably less than 5 percent by weight and most preferably less than 2 percent by weight of Low Molecular Weight acrylic Monomer having a gram molecular weight of less than 200.

DETAILED DESCRIPTION OF THE INVENTION

A preferred embodiment of the invention is now described with more particular reference to a dental prosthesis made of polymeric material. The polymeric material is formed from a polymeric particles and at least one polymerizable Monomer having at least one or more preferably at least two acrylic moieties, and a gram molecular weight of at least 200 and more preferably at least 300. The polymeric material has an unnotched Izod impact strength of at least 2.5 and more preferably at least 3.0 ft.lb/in as measured by Modified ASTM D256, and a flexural fatigue life of at least 20,000 flexes to failure as measured by the Flexural Fatigue of Denture Base Test. Preferably the polymerizable Monomer has a vapor pressure less than 5 mm Hg at 23° C.

Preferably compositions in accordance with the invention have less than one percent by weight of Low Molecular Weight acrylic Monomers; more preferably compositions in accordance with the invention are substantially free of all Low Molecular Weight acrylic Monomers.

In accordance with a preferred embodiment of the invention a denture flask is prepared for subsequent denture fabrication by the lost-wax technique following ordinary techniques by those skilled in the art. The denture mold is coated with separating agents, such as, Al-Cote® separating agent and/or Dent-Kote® separating agent, each sold by Dentsply International, Inc. Methyl methacrylate or other bonding agent is applied to the plastic teeth as the bonding agent. The mold is preferably made from Castone® Dental Stone, sold by Dentsply. The mold is placed in a metal container referred to as a flask. The mold contained within the flask is then packed with the one-component (ready-to-use) heat-curable denture base material in accordance with the invention. The mold is closed and pressed to complete the compression-pack step. After clamping in a spring clamp, the mold is placed into a curing tank. The cure cycle is one and one half hours at 163° F.(73° C.) followed by a ½ hour at 212° F. (100° C.). After removing the cured denture from the mold (de-flasking), the denture is finished (trimmed and polished).

The heat-curable denture material of the invention preferably forms a composite comprised of polymer particles and may include submicron silica filler in an acrylourethane resin matrix. The filler serves to increase viscosity and provide useful characteristics of the composition. Useful heat-cure initiators include dibenzoyl peroxide (BPO), tert-butyl perisononanoate (TBPIN) and/or benzopinacole.

Polymerization of compositions in accordance with the invention is preferably initiated at a temperature of about 115° F. to 240° F., more preferably from about 140° F. to 220° F. and most preferably from about 160° to 212° F. The polymerization (heat cure) time is preferably from about 15 minutes to about 24 hours, more preferably from about 30 minutes to about 15 hours, and most preferably from about 1 hour to about 9 hours. Polymerization of compositions in accordance with the invention is preferably initiated at a temperature of about 163° F. when using benzyl peroxide (BPO) as the catalyst and at a temperature of about 212° F. when using TBPIN/benzopinacole as the catalyst. Polymerization is preferably initiated in a cure tank containing hot water. Preferably solid catalysts, such as BPO have a particle size of less than 20 microns. More preferably the catalyst(s) have a particle size of less than 15 microns.

TBPIN/benzopinacole are preferred catalysts for increased thermal stability. The denture composition of the invention is preferably provided in bulk packaging, for example, 300 to 500 grams of the denture material.

Polymerizable acrylic compounds useful in accordance with the invention include compounds within the scope of general formula (I) of which have a gram molecular weight of at least 200 and more preferably at least 300 are adapted to form polymeric material having an unnotched Izod impact strength of at least about 3.0 ft.lb/in and more preferably at least 3.5 ft.lb/in most preferably at least 4.0 ft.lb/in as measured by Modified ASTM D256:

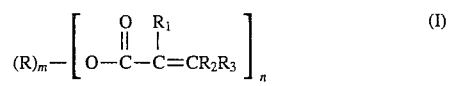

$$(R)_m - \left[ O - \overset{O}{\underset{\|}{C}} - \overset{R_1}{\underset{|}{C}} = CR_2R_3 \right]_n \quad (I)$$

wherein R is an acrylic-free organic moiety which is at least 60 grams per molecule, $R_1$ is hydrogen, halogen, alkyl, substituted alkyl or cyano radical, $R_2$ and $R_3$ each independently is hydrogen or halogen and n is an integer from 1 to 6 and m is an integer from 1 to 1000, R is a organic spacer unit such as one or more of alkyl, cycloaliphatic, aryl, polyether, urethane, polyurethane or polyester, including forms thereof substituted with one or more halogen atoms, carboxyl, phosphoric and other acid moieties and esters and salts thereof. Preferably m is one.

Preferred monomers, oligomers and prepolymers for use in accordance with the invention includes acrylated polyurethane oligomers with polyester or polyether soft segments and cycloaliphatic urethane hard segments, urethane di(meth)acrylates and low viscosity (less than 1,000 cps at 23° C.) diluent monomers. Polymerizable acrylated polyurethane oligomers are waxy, syrupy or mobile liquids. In a preferred embodiment of the invention a poymerizable dental paste composition includes at least one acrylated polyurethane monomer, oligomer, or prepolymer, such as Uvithane 783, Uvithane 893 or Uvithane 892 each sold by Morton International; or Craynor CN 961, Craynor CN 962, Craynor CN 963, Craynor CN 964, Craynor CN 966, Craynor CN 971, Craynor CN 973, Craynor CN 980 or Craynor CN 981 sold by Sartomer, and Mhoromer 6661-0 (chemical name:

7,7,9-trimethyl-4,13-dioxo-3,14-dioxa-5,12-diazahexadecane-1,16-diol dimethacrylate) sold by Rohm Tech. In a preferred embodiment, the composition includes one or more of the following diluent monomers, ethoxylated (3 moles of —$CH_2CH_2O$— per molecule) trimethylolpropane triacrylate (sold as SR454 by Sartomer), isodecyl methacrylate, 1,6-hexanediol dimethacrylate, trimethylolpropane polyoxypropylene triacrylate (6 to 9 moles of —$CH_2CH_2CH_2O$— per molecule, for example, Sartomer CD 501 is 6 mole material), trimethylolpropane polyoxyethylene triacrylate (6 to 9 moles of —$CH_2CH_2O$— per molecule, for example, SR 499 is 6 mole material and SR 502 is the 9 mole material) and tridecyl methacrylate. Methacrylate homologs are suitable as well as acrylates. Preferably less than 30 percent by weight of low viscosity diluent monomers are added to polymerizable compositions in accordance with the invention, to adjust the resin matrix viscosity or improve the impact strength and flexural fatigue life.

The dental composition of the invention has unlimited work time, and forms polymeric products which are non-porous (no air is entrapped) and have low polymerization shrinkage.

Polymerizable acrylic compounds useful to provide polymerizable paste compositions in accordance with the invention include monofunctional monomers and multifunctional oligomers and/or monomers having di- or polyfunctional moieties which are capable of free radical, addition polymerization. In general, preferred reactive functionalities which serve as active sites for polymerization are acrylic. Monofunctional monomers include cyclohexyl methacrylate, benzyl methacrylate, methacrylate, t-butyl methacrylate, n-butyl methacrylate, isobutyl methacrylate, isodecyl methacrylate and 2-ethylhexyl methacrylate. Suitable multifunctional monomers and oligomers may be selected from numerous families of polyfunctional free radical-polymerizable monomers such as acrylic and lower alkyl-acrylic acid diesters, formed from alcohols which have a different reactive functional groups, such as carboxyl and hydroxyl groups, also useful are urethane diacrylates and dimethacrylates, polyvinylic compounds, divinyl aromatic compounds, and others as will be apparent to those skilled in the art.

Preferred, multifunctional monomers and oligomers useful as polymerizable acrylic compounds in polymerizable paste compositions of the invention include esters of unsaturated acids, e.g., acrylic, methacrylic, ethacrylic, propacrylic, butacrylic, maleic, fumaric, citraconic, mesaconic, itaconic, malonic, or aconitic, acids. Other unsaturated acids will be readily apparent to those skilled in the art. These acids are preferably reacted with either saturated or unsaturated polyhydroxylic alcohols to form esters which are effective multifunctional monomers and oligomers useful in the formulation of the compositions of the invention. In general, these alcohols have one or more hydroxylic functionality and have from 2 to about 30 carbon atoms. Thus, useful alcohols include allyl, methallyl, crotyl, vinyl, butenyl, isobutenyl, and similar unsaturated alcohols as well as polyols such as ethylene glycol, propylene glycol, butylene glycol, diethylene glycol, triethylene glycol, tetraethylene glycol, pentaethylene glycol, glycerol, 1,3,3-trimethylolpropane, pentaerythritol, dihydroxyphenol, and alkylidene bisphenols such as bisphenol-A, 1,1-bis (4-hydroxyphenyl) methane, 4,4'-dihydroxybiphenyl, 4,4'-dihydroxydiphenyl sulfone, dihydroxydiphenyl ether, dihydroxydiphenyl sulfoxide, resorcinol, hydroquinone, etc.

Preferred multifunctional monomers and oligomers useful as polymerizable acrylic compounds in polymerizable paste compositions of the invention include the esters of a monomeric unsaturated acids with an unsaturated mono-hydroxylic alcohol such as allyl acrylate, allyl methacrylate, dimethallyl fumarate, N-allyl acrylamide, crotyl acrylate, allyl crotonate, allyl cinnamate and diallyl maleate. Other preferred species are the di-, tri-, and higher esters of polyhydroxylic alcohols such as ethylene glycol diacrylate, trimethylolpropane tri(meth)acrylate, and the dimethacrylate ester of bisphenol-A as well as other acrylate and alkyl acrylate esters. Furthermore, mixtures of multifunctional monomers and/or oligomers are useful in the practice of the invention.

Polymerizable acrylic compounds such as bis-GMA and the urethane dimethacrylate formed from the reaction of hydroxyethyl acrylate, hydroxypropyl acrylate, and their methacrylate homologs with 2,2,4-trimethylhexyl-1,6-diisocyanate (hereinafter referred to as "urethane dimethacrylate" or "urethane diacrylate") are useful. Other diluent monomers which are useful are ethylene glycol dimethacrylate, 1,6-hexanediol dimethacrylate, ethoxylated trimethylolpropane trimethacrylate and the dimethacrylate ester of bisphenol-A and urethane adducts thereof. The corresponding acrylates are similarly useful.

Polymerizable acrylic compounds which are especially useful are oligomers are acrylated polyurethanes (also known as acrylourethane resins (or oligomers)). Preferably, the soft segment of the backbone contains polyester or polyether moiety. Preferably, the hard or urethane segment contains cycloaliphatic groups. Molecular weight of the oligomer is preferably greater than 300 g mol$^{-1}$, more preferably is greater than 400 g mol$^{-1}$ and most preferably greater than 600 g mol$^{-1}$ with molecular weight of oligomer of more than 1,000 g mol$^{-1}$ or more than 5,000 g mol$^{-1}$ providing further reduced volatility.

In a preferred embodiment of the invention, polymerizable acrylic compounds useful in dental compositions in accordance with the invention are vinyl urethane or urethane-(meth)acrylate monomer or prepolymer materials (also known as acrylourethane resins) within the scope of the structural formula (II):

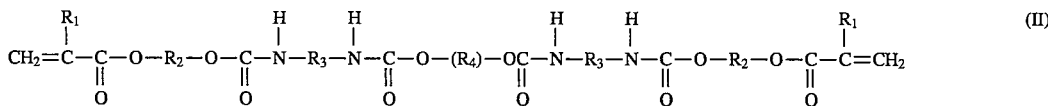

wherein each $R_1$ independently, is hydrogen, halogen, alkyl, substituted alkyl or cyano moiety, each $R_2$ independently is alkylene, substituted alkylene, cycloalkylene, substituted cycloaklylene, arylene or substituted arylene, each $R_3$ independently is alkylene, substituted alkylene, cycloalkylene, arylene, substituted arylene, heterocyclic or substituted heterocyclic, and $R_4$ is a polyester or polyether moiety (backbone or soft segment);

In a preferred embodiment of the invention, polymerizable acrylic compounds useful in dental compositions in accordance with the invention are vinyl urethane or urethane-(meth)acrylate monomer or prepolymer materials (also known as acrylourethane resins) characterized by the structural formula (III):

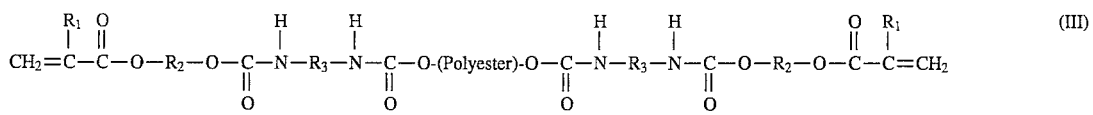

wherein each $R_1$ independently, is hydrogen, alkyl or substituted alkyl, $R_3$ and $R_4$, each independently, is alkyl, substituted alkyl, alkylene, substituted alkylene, cycloalkylene, substituted cycloaklylene, arylene or substituted arylene.

Preferred rubber impact modifiers for use in polymerizable compositions in accordance with the invention include acrylic rubber modifier (Paraloid KM 334 manufactured by Rohm and Haas is an example) and methacrylated butadiene-styrene rubber modifiers (Metablen C223 produced by Elf Atochem is an example). The rubber modifiers, such as rubbery particles, are preferably added to either the resin matrix or the polymeric filler. Addition of rubbery particles to resin is disclosed by Cornell U.S. Pat. No. 3,427,274.

Preferred stabilizers are butylated hydroxytoluene and the methyl ether of hydroquinone (MEHQ).

Compositions in accordance with the invention preferably include fillers, pigments, plasticizers, stabilizers and components of polymerization catalyst system. The fillers preferably include both organic and inorganic particulate fillers to reduce polymerization shrinkage and modify the viscosity characteristics and improve handling and molding characteristics. For example, combinations of fumed and/or ground silica or other inorganic glasses, such as, aluminosilicate glasses known to those skilled in the dental art, may be used with organic fillers to increase viscosity and reduce tack as well as retain its prepolymerized molded shape.

Preferred fillers useful in the paste compositions of the invention include organic fillers such as particulate polymer, and inorganic filler such as glass, ceramic, or glass ceramic.

Preferably the organic filler has a particle size of less than about 200 μm, more preferably less than about 150 μm and most preferably less than about 80 μm. Organic fillers include natural and synthetic polymers and copolymers which preferably are formed by atomization techniques, emulsion polymerization, bulk polymerization or suspension polymerization. In accordance with a preferred embodiment of the invention the organic filler used is a particulate polymer containing a comonomer or rubber impact modifier which will increase the mechanical properties of the resin matrix. Preferred rubber modifiers for a poly methyl methacrylate filler are methacrylated butadiene styrene materials. The organic filler polymer particles, preferably used in the compositions which form polymeric products having in order of increasing preference greater than 50,000; 100,000; 150,000; or 200,000 flexes to failure and more preferably more than 300,000 flexes to failure are discrete, non-crosslinked polymer particles which are swellable in the polymerizable Monomer at temperatures of about 15°–70° C. More preferably, the nonocrosslinked polymer particles are alkyl methacrylate or acrylate polymers or copolymers which are swellable by the polymerizable Monomer at about temperatures of about 20°–50° C. Most preferably, the non-crosslinked polymer particles are copolymers of methyl methacrylate and ethyl methacrylate which are swellable by the polymerizable Monomer at temperatures of about 23°–45° C. The particle size of the fillers may be reduced by ball milling, shearing or by atomization.

Inorganic fillers are produced by fusion or sol gel techniques and their particle size may be reduced by ball milling, attritor milling, atomization, attention milling or precipitation. Preferred inorganic fillers include silica, quartz, borosilicates, silicious fillers, inorganic glasses, such as barium aluminum silicate, lithium aluminum silicate, strontium, lanthanum, and tantalum aluminosilicate glasses. A preferred inorganic filler is microfine amorphous silicon dioxide particulate. Silanated inorganic fillers are considered for purposes of this invention to be inorganic fillers and are also preferred. Silanated means that some of the silanol groups have been substituted or reacted with, for example, dimethyldichlorosilane to form a hydrophobic filler. The inorganic filler can also be coated with gamma methacryloxypropyl trimethoxy silane as a means of "silanating" the surface.

Preferably surface treated polymeric organic particles useful as filler in compositions in accordance with the invention have been treated with a fluorine containing gas as disclosed by Bauman et al in U.S. Pat. No. 4,771,110 incorporated herein by reference in its entirety to generate functional reactive sites in the surface layer of the particles.

Preferably the containers used to enclose polymerizable compositions in accordance with the invention are generally cylindrical and have an oxygen permeability coefficient of at least about $0.4 \times 10^{-10} cm^2/sec$ (cm Hg). Preferably at least a 200 g quantity of polymerizable paste composition is enclosed in such container and has a shelf life of at least about one year.

Preferably dental prostheses made in accordance with the invention are substantially porosity-free. Dental prostheses are preferably formed in molds in accordance with the invention by compression molding, injection molding, pour molding or casting, such as spin casting.

Preferably, polymerizable dental compositions in accordance with the invention include from about 2 to about 95 percent by weight filler; from about 0.5 to about 50 percent by weight inorganic filler, from about 10 to about 90 percent by weight of polymerizable compounds; from about 5 to about 80 percent by weight of acrylic Monomers having a gram molecular weight in order of increasing preference of more than 200, 300, 400, 500, 1,000 or 5,000; less than about 10 percent by weight of Volatile polymerizable compounds; less than about 5 percent by weight of Low Molecular Weight polymerizable compounds.

More preferably, polymerizable dental compositions in accordance with the invention include from about 10 to about 80 percent by weight filler; from about 7 to about 30 percent by weight inorganic filler, from about 20 to about 80 percent by weight of polymerizable compounds; from about 7 to about 70 percent by weight of acrylic Monomers having a gram molecular weight greater than 300; less than about 5 percent by weight of Volatile polymerizable compounds; less than 2 percent by weight of Low Molecular Weight polymerizable compounds.

Especially preferred, polymerizable dental compositions in accordance with the invention include from about 20 to about 70 percent by weight filler; from about 7 to about 15 percent by weight inorganic filler, from about 30 to about 70 percent by weight of polymerizable compounds; from about 10 to about 60 percent by weight of acrylic Monomers having a gram molecular weight greater than 300; less than about 1 percent by weight of Volatile polymerizable compounds; less than about 1 percent by weight of Low Molecular Weight polymerizable compounds.

Polymerizable compositions in accordance with the invention desirably include from 3 to 90 percent by weight of polymer particles which include rubber. Polymerizable compositions in accordance with the invention preferably include from 15 to 75 percent by weight of polymer particles which include rubber. Polymerizable compositions in accordance with the invention more preferably include from 25 to 65 percent by weight of polymer particles which include rubber. Polymerizable compositions in accordance with the invention most preferably include from 35 to 55 percent by weight of polymer particles which include rubber. Preferably the composition is shelf stable, having a mass of from at least 200 g, and the polymerizable acrylic compound is effectively maintained without polymerization for at least six months at 23° C.

In accordance with a preferred embodiment of the invention is provided a shelf stable one-component heat curable polymerizable dental paste composition inlucing at least 5 percent by weight (and more preferably 10 percent by weight) of an acrylic Monomer having a gram molecular weight in order of increasing preference of at least 200, 400 or 1,000, at least 10 percent by weight of polymeric particles and a catalyst. These particles are effectively uncrosslinked polymer particles. The catalyst is adapted to generate free radicals during the heating curing. The composition is adapted to form a polymeric material having a flexural fatigue life of at least 50,000 flexes to failure determined by Flexural Fatigue of Denture Bases Test. Preferably the uncrosslinked polymeric particles are swollen by the acrylic Monomer during heat curing for from about 0.25 hour to about 24 hours at from about 115° F. to about 240° F. and said polymeic material has an unnotched Izod impact strength of at least about 3.0 ft.lb/in as measured by Modified ASTM D256 and a flexural fatigue life of at least 100,000 flexes to failure determine by Flexural Fatigue of Denture Bases Test.

EXAMPLE 1A

Comparative Denture Base

Lucitone 199® denture base material, sold by Dentsply International, Inc., is mixed according to the manufacturers instructions as follows: 21 grams of Lucitone 199® denture base (sold by Dentsply International Incorporated, York, Pa.) polymer powder (shade Light Reddish Pink) is hand spaluated with 10 ml of Lucitone® liquid monomer to produce a fluid resin which contains about 30% by weight methyl methacrylate. The fluid resin is allowed to stand at room temperature for about 10 to 15 minutes until it becomes a "packable" dough that can be handled without sticking to the technician's hands. This dough is molded in a denture flask by compression-packing the flask in a press. Then the flask is closed in a spring clamp and immersed in a hot water curing tank. Full or complete cure is achieved with a cure cycle of 163° F. for one and one half hours followed by ½ hour boil (212° F.) to produce a polymeric denture base with a flexural strength of 13,600 psi, a deflection of 0.384 inches, a modulus of elasticity of 343,000 psi, and an unnotched Izod impact strength of 4.5 ft.lb/in. as shown in Table 2.

Example 1B

Comparative Denture Base

Hi-i® denture base material, sold by Fricke Dental Manufacturing Company, Villa Park, Ill. is mixed according to the manufacturers instructions as follows: 30 ml of Hi-i® denture base polymer powder (shade Special Fibered #1) is hand spaluated with 8.5 ml of Vitacrilic® Cross Link Monomer liquid (sold by Fricke Dental Manufacturing Company, Villa Park, Ill.) to produce a fluid resin which contains at least 20% by weight methyl methacrylate. The fluid resin is allowed to stand at room temperature for 10 minutes until it becomes a "packable" dough. This dough is molded in a denture flask by compression packing the flask in a press, Then the flask is closed in a spring clamp and immersed in a hot water curing tank at 165° F. for 1½ hours followed by a ½ hour at 212° F. boil to produce a polymeric denture base with a flexural strength of 12,500 psi, a deflection of 0.236 inches, a modulus of elasticity of 385,000 psi, and an unnotched Izod impact strength of 3.1 ft.lbs/inch as shown in Table 2.

Example 1C

Comparative Denture Base

Triad® VLC Denture Base and Orthodontic Material sold by Dentsply International, Inc., York, Pa. is used according to the manufacturers instructions as follows: A 16 g sheet of Triad® VLC Denture Base & Orthodontic Material is molded into the form of a denture in a denture flask, and then light cured in a Triad® 2000™ curing unit (sold by Dentsply International Incorporated.) for 11 minutes. The denture formed has a flexural strength of 13,000 psi, a deflection of 0.18 inches, a modulus of elasticity of 505,000 psi and an unnotched Izod impact strength of 1.8 ft.lbs/in as shown in Table 2.

Example 1D

Comparative Crown and Bridge Material

Triad® VLC (Visible light curable) Provisional Material for crowns, bridges, veneers, inlays and onlays is sold by Dentsply International Inc, contains 4.8% by weight of a polyester urethane acrylate sold by Morton International which may have a molecular weight greater than 600 grams per mole. The Triad® VLC Provisional Material is used according to the manufacturer's instructions to produce a provisional crown (a temporary crown for use up to 30 days.). The one component Triad®, VLC Provisional Material is placed into a transparent crown form (which was previously shaped against a stone model of the mouth using a vacuum forming machine). Seat the transparent crown form and the Triad® VLC material firmly on the cast to shape the restoration, then cure (polymerize) in a Triad® Light Curing Unit for a total of 10 minutes. Trim and polish to complete the provisional restoration. The polymeric crown material has a flexural strength of 13,000 psi, a deflection of 0.19 inches, and an unnotched Izod impact strength of 2.0 ft lbs/inch, as shown in Table 2.

Example 1E

Comparative Orthodontic Material

Triad® TranSheet Translucent Light Cure Material is sold by Dentsply International Inc for fabrication of orthodontic appliances and other removable prosthodontic appliances. The Triad® TranSheet material contains 6.1% by weight of a polyester urethane acrylate sold by Morton International which may have a molecular weight greater than 600 grams per mole. TranSheet is used according to manufacturer's instructions to produce an orthodontic appliance: 1) position the orthodontic wires onto a stone cast of the patient's mouth, 2) place a single sheet of TranSheet onto the stone cast and mold with finger pressure into the desired shape, 3) place the cast and TranSheet material into a Triad® Light Curing Unit and cure for 4 minutes to partially polymerize the material, 4) remove the appliance from the cast and apply a thin layer of Triad® Air Barrier Coating to all surfaces of the TranSheet material, 5) place the appliance back into the Triad® Light Curing Unit for 6 additional minutes to complete the cure, and 6) trim and polish to complete the appliance. The polymeric orthodontic material has a flexural strength of 13,800 psi, a deflection of 0.18 inches, a flexural modulus of elasticity of approximately 450,000 psi and an un-notched Izod impact strength of 1.8 ft lb/inch, as shown in Table 2.

Example 1F

Comparative Custom Impression Tray Material

Triad® VLC (visible light curable) Custom Tray Material is sold by Dentsply International Inc for fabrication of custom fit dental impression trays. The Triad® VLC Custom Tray material contains 23.56% by weight polyester urethane acrylate sold by Morton International which may have a molecular weight greater than 600 grams per mole. Triad® Custom Tray material is used according to manufacturer's instructions to produce an impression tray. Prepare a stone cast (model) of patient's mouth and block-out the undercuts and vacant tooth spaces to prevent Tray Material intrusion. After applying a release agent to the cast's surface, adapt (place by hand) a sheet of the Triad® VLC Custom Tray Material to the cast to form the custom-fit impression tray. Place the cast with the adapted tray into a Triad® Light Curing Unit and cure for 2 minutes to partially polymerize the material. Afterwards remove the tray from the cast and apply the thin layer of Triad® Air Barrier Coating to all surfaces of the tray, then cure an additional 6 minutes in the Triad® Light to complete the polymerization. Finish the custom tray by washing in tap water and adjusting the borders for best fit with a carbide bur. The polymeric VLC custom tray material has a flexural strength of 7210 psi, a deflection of 0.16 inches, a flexural modulus of elasticity of 387,000 psi, and an unnotched Izod impact strength of 1.3 ft. lb/inch, as shown in Table 2.

Example 1G

Comparative Denture Base

Hy-pro™ Lucitone® denture base material, sold by Dentsply International Inc., is mixed according to the manufacturer's instructions as follows: 21 grams of Hy-pro™ Lucitone® denture base polymer powder (shade Fibered Light) is hand spatulated with 10 mL of Lucitone® liquid monomer (sold by Dentsply International Inc.) to produce a fluid resin which contains about 30% by weight methyl methacrylate. The fluid resin is allowed to stand at room temperature for about 3 minutes until it becomes a "packable" dough that can be handled without sticking to the technician's hands. This dough is molded in a denture flask by compression-packing the flask in a press. Then the flask is closed in a spring clamp and immersed in a hot water curing tank. Full (complete) cure is achieved with a cure cycle of 163° F. for 1½ hours followed by ½ hour boil (212° F.) to produce a polymeric denture base with a flexural strength of 12,100 psi, a deflection of 0.21 inches, a modulus of elasticity of 392,000 psi, and an unnotched Izod impact strength of 2.9 ft lb/in as shown in Table 2.

Example 1H

Comparative Denture Base

Triad Prototype visible light curable material produced by Wilson et al is used to form a denture as follows: The Triad Prototype paste material is molded into the form of a denture in a denture flask, then light cured in a Triad® Light Curing Unit. The denture formed during this procedure has a flexural fatigue life of 8787 flexes to failure at 0.1 inch deflection (or bend distance) as is shown in Table 2.

Example 1

Denture Base 38.77 g of cycloaliphatic polyester urethane acrylate CN964 (Sartomer), 6.84 g of isodecyl methacrylate, 0.4 g of dibenzoyl peroxide, 0.019 g of butylated hydroxytoluene, 0.008 g of gamma-methacryloxypropyltrimethoxysilane, 45.41 g of poly(methyl methacrylate-co-ethyl methacrylate:54.5:45.5), 5.27 g of non-silanated, fumed silica (Aerosil 200 sold by DeGussa Corp.), 3.21 g of silanated, fumed silica (Aerosil R972 sold by DeGussa Corp.), 0.0514 g of red acetate fibers, 0.0017 g of Ultramarine Blue BC 7104 (sold by Whittaker, Clarke & Daniels, Inc., South Plainfeld, N.J.), 0.00059 g of Black Irox 7053 (sold by Whittaker, Clarke & Daniels, Inc.), 0.00153 g of Cromophtal Scarlet RS (sold by Ciba Geigy Corp.), 0.000592 g of Cromophtal Red BRN (sold by Ciba Geigy Corp.) and 0.0177 g of Titanox 328 (sold by Whittaker, Clarke & Daniels, Inc.) are mixed to form a one component heat-curable denture base composition. The one component heat-curable denture base composition is molded in a denture flask, and the flask is immersed in water at 163° F. for 1½ hours and then at 212° F. for ½ hour to form a polymeric denture base having a flexural yield strength of 4,400 psi, a deflection at yield of 0.45 inch, a modulus of elasticity of 98,000 psi and an unnotched Izod impact strength of 4.0 ft lbs./in, as shown in Table 2.

Example 2

Denture Base 38.77 g of cycloaliphatic polyester urethane acrylate CN964 (Sartomer), 6.84 g of isodecyl methacrylate, 0.4 g of dibenzoyl peroxide, 0.019 g of butylated hydroxytoluene, 0.008 g of gamma-methacryloxypropyltrimethoxysilane, 45.41 g of poly(methyl methacrylate-co-ethyl methacrylate:54.5:45.5), 5.27 g of non-silanated, fumed silica, 3.21 g of silanated, fumed silica, 0.0514 g of red acetate fibers, 0.0017 g of Ultramarine Blue BC 7104, 0.00059 g of Black Irox 7053, 0.00153 g of Cromophtal Scarlet RS, 0.000592 g of Cromophtal Red BRN and 0.0177 g of Titanox 328 are mixed to form a one component heat-curable denture base composition. The one component heat-curable denture base composition is molded in a denture flask, and the flask is immersed in boiling water at 212° F. for 1 hour to form a polymeric denture base having a flexural yield strength of 4,720 psi, a deflection at yield of 0.46 inch, a modulus of elasticity of 108,000 psi and an unnotched Izod impact strength of 5.4 ft lbs./in, as shown in Table 2.

Example 3

Denture Base 38.77 g of cycloaliphatic polyester urethane acrylate CN964, 6.84 g of isodecyl methacrylate, 0.4 g of dibenzoyl peroxide, 0.019 g of butylated hydroxytoluene, 0.008 g of gamma-methacryloxy propyltrimethoxy silane, 45.41 g of poly(methyl methacrylate-co-ethyl methacrylate:54.5:45.5), 5.27 g of non-silanated, fumed silica, 3.21 g of silanated, fumed silica, 0.0514 g of red acetate fibers, 0.0017 g of Ultramarine Blue BC 7104, 0.00059 g of Black Irox 7053, 0.00153 g of Cromophtal Scarlet RS, 0.000592 g of Cromophtal Red BRN and 0.0177 g of Titanox 328 are mixed to form a one component heat-curable denture base composition. The one component heat-curable denture base composition is molded in a denture flask, and the flask is immersed in boiling water at 212° F. for 1½ hour to form a polymeric denture base having a flexural yield strength of 4,050 psi, a deflection at yield of 0.46 inch, a modulus of elasticity of 98,700 psi and an unnotched Izod impact strength of 5.2 ft lbs./in, as shown in Table 2.

Example 4

Denture Base 38.77 g of cycloaliphatic polyester urethane acrylate CN964, 6.84 g of isodecyl methacrylate, 0.4 g of dibenzoyl peroxide, 0.019 g of butylated hydroxytoluene, 0.008 g of gamma-methacryloxy propyltrimethoxysilane, 45.41 g of poly(methyl methacrylate-co-ethyl methacrylate:54.5:45.5), 5.27 g of non-silanated, fumed silica, 3.21 g of silanated, fumed silica, 0.0514 g of red acetate fibers, 0.0017 g of Ultramarine Blue BC 7104, 0.00059 g of Black Irox 7053, 0.00153 g of Cromophtal Scarlet RS, 0.000592 g of Cromophtal Red BRN and 0.0177 g of Titanox 328 are mixed to form a one component heat-curable denture base composition. The one component heat-curable denture base composition is molded in a denture flask, and the flask is immersed in water at 163° F. for 1½ hour and then at boil (212° F.) for 1½ hour to form a polymeric denture base having a flexural yield strength of 4,600 psi, a deflection at yield of 0.46 inch, a modulus of elasticity of 108,000 psi and an unnotched Izod impact strength of 4.4 ft lbs./in, as shown in Table 2.

Example 5

Denture Base 38.69 g of cycloaliphatic polyester urethane acrylate CN964 (Sartomer), 6.84 g of isodecyl methacrylate, 0.24 g of tert-butyl perisononanoate, 0.24 g of benzopinacole, 0.019 g of butylated hydroxytoluene, 0.008 g of gamma-methacryloxypropyltrimethoxy silane, 45.6 g of poly(methyl methacrylate-co-ethyl methacrylate:54.5:45.5), 5.14 g of non-silanated, fumed silica and 3.21 g of silanated, fumed silica are mixed to form a one component heat-curable denture base composition. The one component heat-curable denture base composition is molded in a denture flask, and the flask is immersed in boiling water at 212° F. for 1 hour boil to form a polymeric denture base having a flexural yield strength of 4,390 psi, a deflection at yield of 0.44 inch, a modulus of elasticity of 109,000 psi and an unnotched Izod impact strength of 3.7 ft lbs./in, as shown in Table 2.

Example 6

Denture Base 38.69 g of cycloaliphatic polyester urethane acrylate CN964 (Sartomer), 6.84 g of isodecyl methacrylate, 0.24 g of tert-butyl perisononanoate, 0.24 g of benzopinacole, 0.019 g of butylated hydroxytoluene, 0.008 g of gamma-methacryloxypropyltrimethoxy silane, 45.6 g of poly(methyl methacrylate-co-ethyl methacrylate:54.5:45.5), 5.14 g of non-silanated, fumed silica and 3.21 g of silanated, fumed silica are mixed to form a one component heat-curable denture base composition. The one component heat-curable denture base composition is molded in a denture flask, and the flask is immersed in boiling water at 212° F. for 1½ hours boil to form a polymeric denture base having a flexural yield strength of 4,310 psi, a deflection at yield of 0.46 inch, a modulus of elasticity of 103,000 psi and an unnotched Izod impact strength of 4.2 ft lbs./in, as shown in Table 2.

Example 7

Denture Base 38.69 g of cycloaliphatic polyester urethane acrylate CN964 (Sartomer), 6.84 g of isodecyl methacrylate, 0.24 g of tert-butyl perisononanoate, 0.24 g of benzopinacole, 0.019 g of butylated hydroxytoluene, 0.008 g of gamma-methacryloxypropyltrimethoxy silane, 45.6 g of poly(methyl methacrylate-co-ethyl methacrylate:54.5:45.5), 5.14 g of non-silanated, fumed silica and 3.21 g of silanated, fumed silica are mixed to form a one component heat-curable denture base composition. The one component heat-curable denture base composition is molded in a denture flask, and the flask is immersed in water at 163° F. for 1½ hours and then at 212° F. for 1½ hours to form a polymeric denture base having a flexural yield strength of 5,160 psi, a deflection at yield of 0.46 inch, a modulus of elasticity of 125,000 psi and an unnotched Izod impact strength of 4.7 ft lbs./in, as shown in Table 2

Example 8

Denture Base 34.2 g of cycloaliphatic polyester urethane acrylate CN964 (Sartomer), 11.4 g of trimethylolpropane polyoxypropylene triacrylate CD501 (sold by Sartomer), 0.4 g of dibenzoyl peroxide, 0.02 g of butylated hydroxytoluene, 0.008 g of gamma-methacryloxypropyltrimethoxysilane, 45.6 g of poly(methyl methacrylate-co-ethyl methacrylate:54.5:45.5), 5.13 g of non-silanated, fumed silica and 3.21 g of silanated, fumed silica are mixed to form a one component heat-curable denture base composition. The one component heat-curable denture base composition is molded in a denture flask, and the flask is immersed in water at 163° F. for 1½ hours and then at boil (212° F.) for ½ hour to form a polymeric denture base having a flexural yield strength of 5,520 psi, a deflection at yield of 0.439 inch, a modulus of elasticity of 146,500 psi and an unnotched Izod impact strength of 3.8 ft lbs./in, as shown in Table 2.

Example 9

Teeth 26.93 g of cycloaliphatic polyester urethane acrylate CN964 (Sartomer), 6.84 g of cycloaliphatic polyester urethane acrylate CN963 (sold by Sartomer), 11.4 g of trimethylolpropane polyoxy propylene triacrylate CD501 (sold by Sartomer), 0.4 g of dibenzoyl peroxide, 0.02 g of butylated hydroxytoluene, 0.008 g of gamma-methacryloxypropyltrimethoxysilane, 45.6 g of poly(methyl methacrylate-co-ethyl methacrylate:54.5:45.5), 5.13 g of non-silanated, fumed silica and 3.21 g of silanated, fumed silica are mixed to form a tooth material. The tooth material is injected into tooth-shaped cavities in a two-part metal mold by a transfer molding technique at a pressure of 500 psi and cured at a temperature of 250° F. for six minutes to form polymeric teeth. After the heat curing cycle, the metal mold and the teeth are cooled at about 40°–45° F. for six minutes. The polymeric teeth have a modulus of elasticity of 213,000 psi and an unnotched Izod impact strength of 3.1 ft.lb/in, as shown in Table 2.

Example 10

Injection-Molded Denture Base 30 g of one-component heat-curable denture base formed by following Example 1 is injected into a mold contained within a flask, and the flask is immersed in boiling water (212° F.) for ½ hour to form a polymeric denture base.

Example 11

Denture Base

A. Plasma treatment of polymeric filler 131.5 g of poly-(methyl methacrylate-co-ethyl methacrylate: 54.5;45.5) was gas plasma treated to create a bondable (reactive) surface by Advanced Plasma Systems, Inc. (St. Petersburg, Fla.).

B. Preparation of the denture base 45.6 g of plasma treated poly(methyl methacrylate-co-ethyl methacrylate: 54.5:45.5) from section 11(A) was mixed to form a one component, heat-curable denture base material by substituting the plasma treated polymer in Example 1. The one component heat-curable denture base composition is molded in a denture flask, and the flask is immersed in water at 163° F. for 1½ hours and then at 212° F. for ½ hour to form a polymeric denture.

Example 12

Denture Base 32.97g of 7,7,9-trimethyl-4,13-dioxo-3,14-dioxa-5,12-diazahexadecane- 1,16-dioldimethacrylate, 10.0 g of cycloaliphatic polyester urethane acrylate CN 964 (Sartomer), 0.4 g of dibenzoyl peroxide, 0.02 g of butylated hydroxytoluene, 0.01 g of gamma-methacryloxypropyltrimethoxysilane, 47.84 g of poly (methyl methacrylate-co-n butyl methacrylate-co-methacrylated-butadiene styrene rubber: 92.1:2.5:5.4), 5.39 g of non-silanated, fumed silica and 3.37 g of silanated, fumed silica are mixed to form a one component heat-curable denture base composition. The one component heat-curable denture base composition is molded in a denture flask, and the flask is immersed in water at 163° F. for 1½ hours and then at boil (212° F.) for ½ hour to form a polymeric denture base having a flexural strength of 13,900 psi, a deflection at break of 0.32 inch, a modulus of elasticity of 374,000 psi and an unnotched Izod impact strength of 2.8 ft lbs./in, as shown in Table 2.

Example 13

Denture Base 32.97 g of 7,7,9-trimethyl-4,13-dioxo-3,14-dioxa-5,12-diazahexadecane-1,16-dioldimethacrylate, 10.0 g of trimethylolpropane polyoxyethylene triacrylate SR502 (sold by Sartomer), 0.40 g of dibenzoyl peroxide, 0.02 g of butylated hydroxytoluene, 0.01 g of gamma-methacryloxypropyltrimethoxysilane, 47.84 g of poly (methyl methacrylate-co-n butyl methacrylate-co-methacrylated-butadiene styrene rubber: 92.1:2.5:5.4), 5.39 g of non-silanated fumed silica and 3.37 g of silanated, fumed silica are mixed to form a one component heat-curable denture base composition. The one component heat-curable denture base composition is molded in a denture flask, and the flask is immersed in water at 163° F. for 1½ hours and then at boil (212° F.) for ½ hour to form a polymeric denture base having a flexural strength of 14,100 psi, a deflection of break of 0.41 inch, a modulus of elasticity of 376,000 psi and an unnotched Izod impact strength of 4.0 ft.lbs./in, as shown in Table 2.

Example 14

Denture Base 32.97 g of 7,7,9-trimethyl-4,13-dioxo-3,14-dioxa-4,12-diazahexadecane-1,16-dioldimethacrylate, 10.0 g of trimethylolpropane polyoxyethylene triacrylate SR 499 (sold by Sartomer), 0.40 g of dibenzoylperoxide, 0.02 g of butylated hydroxy toluene, 0.01 g of gamma-methacryloxypropyltrimethoxysilane, 47.84 g of poly (methylmethacrylate-co-n butyl methacrylate-co-methacrylated butadiene styrene rubber: 92.1:2.5:5.4), 5.39 g of non-silanated fumed silica and 3.37 g of silanated fumed silica are mixed to form a one-component heat-curable denture base composition, The one component heat-curable denture base composition is molded in a denture flask, and the flask is immersed in water at 163° F. for 1½ hours and then at boil (212° F.) for ½ hour to form a polymeric denture base having a flexural strength of 14,500 psi, a deflection at break of 0.40 inches, a modulus of elasticity of 373,000 psi and an unnotched Izod impact strength of 3.3 ft lbs/in as shown in Table 2.

The composition of Examples 1, 5, 8, and 9 are shown in Table 1. The compositions of Examples 12, 13, and 14 are shown in Table 1A.

TABLE 1

| | Composition of Denture Base | | | | |
|---|---|---|---|---|---|
| | | Example | | | |
| | Composition | 1 | 5 | 8 | 9 |
| Oligomers | cycloaliphatic polyester urethane acrylate (CN964) | 38.77 | 38.69 | 34.2 | 26.93 |

TABLE 1-continued

Composition of Denture Base

| | Composition | Example 1 | Example 5 | Example 8 | Example 9 |
|---|---|---|---|---|---|
| | cycloaliphatic polyester urethane acrylate (CN963) | — | — | — | 6.84 |
| | 7,7,9-trimethyl-4,13-dioxo-3,14-dioxa-5,12-diazahexa-decane-1,16-dioldimethacrylate | — | — | — | — |
| Diluent Monomers | isodecyl methacrylate | 6.84 | 6.84 | — | — |
| | trimethyolpropane polyoxypropylene triacrylate (CD 501) | — | — | 11.4 | 11.4 |
| | trimethylolpropane polyoxyethylene triacrylate (SR502) | — | — | — | — |
| | Trimethylolpropane polyoxyethylene triacrylate (SR499) | — | — | — | — |
| Catalyst | dibenzoyl peroxide | 0.4 | — | 0.4 | 0.4 |
| | tert-butyl perisononanoate | — | 0.24 | — | — |
| | benzopinacole | — | 0.24 | — | — |
| Stabilizer and Coupling Agent | butylated hydroxytoluene | 0.019 | 0.019 | 0.02 | 0.02 |
| | gamma-methacryloxypropyltrimethoxy-silane | 0.008 | 0.008 | 0.008 | 0.008 |
| | (2-hydroxy-4-methoxyphenyl)-benzophenone | — | — | — | — |
| Polymer Particles | poly(methyl methacrylate-co-ethyl methacrylate: 54.5:45.5) | 45.41 | 45.6 | 45.6 | 45.6 |
| | Poly(methyl methacrylate-co-n butylmethacrylate-co-methacrylated butadiene styrene rubber: 92.1:2.5:5.4) | — | — | — | — |
| Filler | non-silanated, fumed silica (Aerosil 200) | 5.27 | 5.14 | 5.13 | 5.13 |
| | silanated, fumed silica (Aerosil R972) | 3.21 | 3.21 | 3.21 | 3.21 |
| Pigments | Red Acetate Fibers | 0.0514 | — | — | — |
| | Ultramarine Blue BC 7104 | 0.0017 | — | — | — |
| | Black Irox 7053 | 0.00059 | — | — | — |
| | Cromophtal Scarlet RS | 0.00153 | — | — | — |
| | Cromophtal Red BRN | 0.000592 | — | — | — |
| | Titanox 328 | 0.0177 | — | — | — |

TABLE 1 A

Composition of Denture Base

| | Composition | Example 12 | Example 13 | Example 14 |
|---|---|---|---|---|
| Oligomers | cycloaliphatic polyester urethane acrylate (CN964) | 10.0 | — | — |
| | cycloaliphatic polyester urethane acrylate (CN963) | — | — | — |
| | 7,7,9-trimethyl-4,13-dioxo-3,14-dioxa-5,12-diazahexa decane-1,16-dioldimethacrylate | 32.97 | 32.97 | 32.97 |
| Diluent Monomers | isodecyl methacrylate | — | — | — |
| | trimethyolpropane polyoxypropylene triacrylate (CD 501) | — | — | — |
| | trimethylolpropane polyoxy ethylene triacrylate (SR502) | — | 10.0 | — |
| | Trimethylolpropane poly oxyethylene triacrylate (SR499) | — | — | 10.0 |
| Catalyst | dibenzoyl peroxide | 0.40 | 0.40 | 0.40 |
| | tert-butyl perisononanoate | — | — | — |
| | benzopinacole | — | — | — |
| Stabilizer and Coupling Agent | butylated hydroxytoluene | 0.02 | 0.02 | 0.02 |
| | gamma-methacryloxypropyl-trimethoxy silane | 0.01 | 0.01 | 0.01 |
| | (2-hydroxy-4-methoxyphenyl) benzophenone | — | — | — |
| Polymer Particles | poly(methyl methacrylate-co-ethyl methacrylate: 54.5:45.5) | — | — | — |
| | Poly(methyl methacrylate-co-n butylmethacrylate-co-methacrylated butadiene styrene rubber: 92.1:2.5:5.4) | 47.84 | 47.84 | 47.84 |
| Filler | non-silanated, fumed silica (Aerosil 200) | 5.39 | 5.39 | 5.39 |
| | silanated, fumed silica (Aerosil R972) | 3.37 | 3.37 | 3.37 |
| Pigments | Red Acetate Fibers | — | — | — |
| | Ultramarine Blue BC 7104 | — | — | — |
| | Black Irox 7053 | — | — | — |
| | Cromophtal Scarlet RS | — | — | — |
| | Cromophtal Red BRN | — | — | — |
| | Titanox 328 | — | — | — |

Table 2 shows the flexural strength, deflection, modulus of elasticity and unnotched Izod impact strength and/or flexural fatigue life for the polymeric products of prior art comparative Examples 1A through 1H as well as Examples 1 through 9 and 12 through 14 in accordance with the invention.

TABLE 2

Physical Properties of Polymeric Dental Products

| Example | Flexural Strength, psi | Deflection, inches at permanent deformation | Modulus of Elasticity, psi | Unnotched Izod Impact Strength, ft · lbs/in | Median number of flexes to failure at 0.1 inch (2.5 mm) deflection (bend distance) | Weight percent of Low Molecular Weight Monomer |
|---|---|---|---|---|---|---|
| 1A | 13,600 | 0.384 | 343,000 | 4.5 | 13,000 | approximately 25 |
| 1B | 12,500 | 0.236 | 385,000 | 3.1 | 19,300 | approximately 25 |
| 1C | 13,000 | 0.18 | 505,000 | 1.8 | 2,747 | 0 |
| 1D | 13,000 | 0.19 | — | 2.0 | estimated to be less than 5,000 | 0 |
| 1E | 13,800 | 0.18 | 450,000 | 1.8 | estimated to be less than 5,000 | 0 |
| 1F | 7,210 | 0.16 | 387,000 | 1.3 | estimated to be less than 5,000 | 0 |
| 1G | 12,100 | 0.21 | 392,000 | 2.9 | 115,700 | approximately 25 |
| 1H | — | — | — | — | 8,787 | 0 |
| 1 | 4,400 | 0.45 | 98,000 | 4.0 | greater than 1,088,000 | 0 |
| 2 | 4,720 | 0.46 | 108,000 | 5.4 | approx. greater than 1,000,000 | 0 |
| 3 | 4,050 | 0.46 | 98,700 | 5.2 | approx. greater than 1,000,000 | 0 |
| 4 | 4,600 | 0.46 | 108,000 | 4.4 | approx. greater than 1,000,000 | 0 |
| 5 | 4,390 | 0.44 | 109,000 | 3.7 | — | 0 |
| 6 | 4,310 | 0.46 | 103,000 | 4.2 | — | 0 |
| 7 | 5,160 | 0.46 | 125,000 | 4.7 | — | 0 |
| 8 | 5,520 | 0.439 | 146,500 | 3.8 | — | 0 |
| 9 | — | — | 213,000 | 3.1 | — | 0 |
| 12 | 13,900 | 0.32 | 374,000 | 2.8 | 26,500 | 0 |
| 13 | 14,100 | 0.41 | 376,000 | 4.0 | 59,500 | 0 |
| 14 | 14,500 | 0.40 | 373,000 | 3.3 | — | 0 |

Some prior art denture base material includes Low Molecular Weight Monomer and forms polymeric material which has more than 50,000 flexes to failure, as is shown in Example 1G. Those Denture base compositions used in the prior art which include at least one polymerizable acrylic Monomer having at least one acrylic moieties and a gram molecular weight of at least about 200 form polymeric material which has less than about 10,000 flexes to failure using the Flexural Fatigue of Denture Bases Test, as is shown in Example 1C. The superior denture base compositions in accordance with the preferred embodiment of the invention include at least one polymerizable acrylic Monomer having at least one and more preferably at least two acrylic moieties and a gram molecular weight of at least 200 and form polymeric material which has more than 20,000 flexes to failure using the Flexural Fatigue of Denture Bases Test.

A preferred embodiment of the invention provides polymeric dental products having an unnotched Izod impact strength preferably of at least 2.5 and more preferably at least 3.0 ft.lbs/in and preferably at least 50,000 flexes to break formed from polymerizable compositions which are free of Low Molecular Weight Monomers. The prior art does not provide polymeric dental products having an unnotched Izod impact strength of at least 3.0 ft.lb/in and at least 50,000 flexes to break formed from a polymerizable composition which is free of Low Molecular Weight Monomer. The polymerizable compositions of prior art comparative Examples 1A, 1B and 1G each contain at least 20 percent of methyl methacrylate which is a Low Molecular Weight Monomer. The polymeric dental products of prior art comparative Examples 1C, 1D, 1E and 1F each have an unnotched Izod impact strength substantially less than 2.5 ft.lb/in, The polymeric dental products of Examples 1D, 1E, and 1F are expected to have less than 5,000 flexes to failure using the Flexural Fatigue of Denture Bases Test due to their low deflection to permanent deformation and similarity of the polymers to that of Example 1C.

The products of the composition in accordance with the invention as exemplified by Example 1 through 8 have bend distance (deflection) to permanent deformation which is higher than the product of prior art Example 1A, 1B, 1C, 1D, 1E, 1F and 1G.

The flexural fatigue life of the products of compositions in accordance with the invention as exemplified by Example 1 are unexpectedly superior to that of all known products of the prior art as exemplified by comparative Examples 1A, 1B, 1C and 1G. The 2.5 mm (0.1 inch) bend distance in the flexural fatigue test is an accelerated test since movement during use in-the-mouth is purportedly less than 1 mm. The more than 1,088,000 flexes to failure for the product of Example 1 on our test machine is comparable to at least several millions of flexes at less than 1 mm of bend in the actual use of a denture. The median number of flexes to failure of the heat-curable denture base material of the invention is an exceptionally high number of bend cycles before breaking compared to the products of prior art denture base materials formed in Examples 1A, 1B, 1C and 1G.

The flexural strengths of the products of the compositions in accordance with the invention as exemplified by Examples 12, 13, and 14 are as high as or higher than prior art Examples 1A, 1B, 1C, 1D, 1E, 1F and 1G. The flexural fatigue lives of the products of Examples 12 and 13 are superior to those of prior art Examples 1A, 1B and 1C.

Heat-curable denture material of the invention preferably includes benzoyl peroxide (BPO), or tert butyl perisononanoate (TBPIN) or benzopinacole.

It should be understood that while the present invention has been described in considerable detail with respect to certain specific embodiments thereof, it should not be considered limited to such embodiments but may be used in other ways without departure from the spirit of the invention and the scope of the appended claims.

We claim:

1. A dental prosthesis comprising polymeric material formed by heat curing a one-component polymerizable composition for from about 0.25 hour to about 24 hour at from about 115° F. to about 240° F. in a chamber of a dental prosthesis mold having an inner wall with a dental prosthesis shape, said composition comprising less than 10 percent by weight of polymerizable acrylic compounds having a gram molecular weight of less than 200, and at least one polymerizable acrylic compound having a gram molecular weight of at least 1,000, said polymeric material having at least about 20,000 flexes to failure using the Flexural Fatigue of Denture Bases Test and an unnotched Izod impact strength of at least 2.5 ft.lb/in as measured by Modified ASTM D256.

2. The dental prosthesis of claim 1 wherein said acrylic compound has at least two acrylic moieties and comprises at least about 5 percent by weight of said polymerizable compounds, and said polymeric material has at least 50,000 flexes to failure using the Flexural Fatigue of Denture Bases Test and an unnotched Izod impact strength of at least 3.0 ft.lb/in as measured by Modified ASTM D256.

3. The dental prosthesis of claim 1 wherein said composition further comprises polymeric particles, said polymeric particles being swollen with said polymerizable acrylic compound during said heat curing, and wherein said polymerizable compounds further comprise less then 30 percent by weight of Volatile compounds having a gram molecular weight of less than 400 and said polymerizable composition further comprises at least 1 percent by weight of polymer particles, said polymer particles, said polymer particles comprise rubber or rubber modifier.

4. The dental prosthesis of claim 1 wherein said polymerizable compounds comprise less than 5 percent by weight of polymerizable acrylic compounds having a gram molecular weight of less than 200.

5. The dental prosthesis of claim 2 wherein said acrylic Monomer comprises at least 10 percent by weight of said polymerizable compounds and said polymerizable composition is heat cured for from about 0.5 hour to about 15 hours at from about 140° F. to about 220° F.

6. The dental prosthesis of claim 2 wherein said polymerizable compounds comprise less than 20 percent by weight of Volatile compounds.

7. The dental prosthesis of claim 2 wherein said polymerizable compounds comprise less than one percent by weight of Low Molecular Weight polymerizable acrylic compounds having a gram molecular weight less than 150.

8. The dental prosthesis of claim 1 wherein said acrylic Monomer comprises at least 20 percent by weight of said polymerizable composition.

9. The dental prosthesis of claim 1 wherein said polymerizable compounds further comprise less then 10 percent by weight of Volatile compounds and said polymeric material has at least 50,000 flexes to failure.

10. The dental prosthesis of claim 1 wherein said polymerizable compound comprise less than 0.5 percent by weight of Low Molecular Weight polymerizable compounds having a gram molecular weight less than 130.

11. The dental prosthesis of claim 1 wherein said prosthesis is a denture base, artificial tooth, filling, crown, bridge or inlay.

12. The dental prosthesis of claim 8 wherein said prosthesis is a denture base artificial tooth, filling, crown, bridge or inlay.

13. The dental prosthesis of claim 1 wherein said composition further comprises polymeric filler particles, and said impact strength is at least 3.5 ft.lb/in as determined by Modified ASTM D256.

14. The dental prosthesis of claim 1 wherein said polymeric material has a flexural fatigue life of at least 1,000,000 flexes to failure determined by Flexural Fatigue of Denture Bases Test.

15. The dental prosthesis of claim 1 wherein said molecular weight of said acrylic Monomer is at least 5,000 g/mol.

16. The dental prosthesis of claim 1 wherein said polymerizable comprises a polymer particles which are swellable by said monomer at about 23° C. and about 760 mm of Hg.

17. A denture base, comprising a polymeric material formed by heat curing a one-component polymerizable composition in a chamber of a mold having an inner wall with a surface which forms the shape of said dental prosthesis, said heat curing being for from about 0.25 hours to about 24 hours at from about 115° F. to about 240° F., said polymerizable composition comprising at least one polymerizable acrylic Monomer having at least two acrylate moieties, and a gram molecular weight of at least about 1,000, said polymeric material having an unnotched Izod impact strength of at least 3.0 ft.lb/in as measured by Modified ASTM D256, a flexural fatigue life of at least 50,000 flexes to failure measured by the Flexural Fatigue of Denture Bases Test.

18. The denture base of claim 17 wherein said polymerizable composition further comprises particles of polymer, said polymer being swellable by said monomer at about 23° C. and about 760 mm Hg.

19. The denture base of claim 17 wherein said molecular weight of said acrylic Monomer is at least 5,000 g/mol.

20. The denture base of claim 17 wherein said acrylic Monomer comprises at least 20 percent by weight of said polymerizable composition.

21. The denture base of claim 17 wherein said acrylic polymerizable composition comprises less than 10 percent by weight of Volatile compounds.

22. A denture comprising:

a denture base and at least one artificial tooth, said denture base comprising a polymeric material having a flexural fatigue life of at least 200,000 flexes to failure determined by the Flexural Fatigue of Denture Bases Test.

23. The denture of claim 22 wherein said polymeric material has a flexural fatigue of at least 300,000 flexes of failure determined by the Flexural Fatigue of Denture Bases Test.

24. A method of making a denture, comprising compression molding while heat curing a one-component polymerizable composition for from about 0.25 hour to about 24 hours at from about 115° F. to about 240° F. while enclosed by a mold chamber wall having a denture shape to form a denture, said polymerizable composition having a polymerizable monomer with a molecular weight greater than about 1,000, a free radical generating catalyst, said acrylic Monomer being adapted to form a polymeric material having an unnotched Izod impact strength of at least about 3.0 ft.lb/in as measured by Modified ASTM D256, and at least 50,000 flexes to failure measured by the Flexural Fatigue of Denture Bases Test.

25. The method of claim 24 wherein said polymeric material has a flexural fatigue of at least 100,000 flexes to failure determined by the Flexural Fatigue of Denture Bases Test.

26. A method of making a denture base, comprising:

heat curing a polymerizable composition having a polymerizable acrylic Monomer having a gram molecular weight of at least about 1,000 for from about 0.25 hour to about 24 hours at from about 115° F. to about 240° F. in a chamber of a dental prosthesis mold with an inner wall having a denture base shape, said acrylic Monomer being adapted to form a polymeric material having an unnotched Izod impact strength of at least about 3.0 ft.lb/in as measured by Modified ASTM D256, and at least 50,000 flexes to failure by the Flexural Fatigue of Denture Bases Test, compression molding and heat curing said polymerizable composition to form a denture base.

27. A method of making a one component denture base, comprising:

heat curing a polymerizable composition having at least 5 percent by weight a polymerizable acrylic Monomer having a gram molecular weight greater than about 1,000 for from about 0.25 hour to about 24 hours at from about 115° F. to about 240° F. in a chamber of a dental prosthesis mold with an inner wall having a denture base shape, said acrylic Monomer being adapted to form a polymeric material having an unnotched Izod impact strength of at least about 3.0 ft.lb/in as measured by Modified ASTM D256, and at least 50,000 flexes to failure by the Flexural Fatigue of Denture Bases Test, molding and heat curing said polymerizable composition to form a denture base.

28. A shelf stable one-component heat curable polymerizable dental paste composition comprising:

at least 5 percent by weight of a polymerizable acrylic compound having a gram molecular weight of at least about 1,000, at least 10 percent by weight of polymeric particles and a catalyst, said composition being adapted to form a polymeric material having a flexural fatigue life of at least about 20,000 flexes to failure determined by Flexural Fatigue of Denture Bases Test, said composition comprising less than 10 percent by weight of monomers having a gram molecular weight less than 200.

29. The composition of claim 28 wherein said composition comprising less than 5 percent by weight of Low Molecular Weight Monomer, said acrylic Monomer has a gram molecular weight of at least 400, said catalyst being adapted to generate free radicals during said heating curing, and said uncrosslinked polymeric particles are swollen or partially dissolved by said acrylic Monomer during heat curing for from about 0.25 hour to about 24 hours at from about 115° F. to about 240° F. and said polymeric material has an unnotched Izod impact strength of at least about 3.0 ft.lb/in as measured by Modified ASTM D256 and a flexural fatigue life of at least 100,000 flexes to failure determined by Flexural Fatigue of Denture Bases Test.

30. The dental composition of claim 28 wherein said polymeric material has a flexural fatigue life of at least 100,000 flexes to failure determine by Flexural Fatigue of Denture Bases Test and an unnotched Izod impact strength of at least 2.5 ft.lb/in as measured by Modified ASTM D256.

31. The dental composition of claim 28 wherein said polymeric material has a flexural fatigue life of at least 150,000 flexes to failure determine by Flexural Fatigue of Denture Bases Test and said composition percent by weight of said acrylic Monomer further comprising of at least 20 and has a vapor pressure of less than 10 mm Hg at 23° C.

32. The dental composition of claim 28 wherein said composition further comprises benzoyl peroxide, tert butyl perisononanoate or benzopinacole, and said composition has a vapor pressure of less than 5 mm Hg at 23° C.

33. The dental composition of claim 28 wherein said composition further comprises pigment.

34. The dental composition of claim 28 wherein said composition is light reddish pink in color.

35. The dental composition of claim 28 wherein said particles are swollen by said acrylic Monomer.

36. The dental composition of claim 28 wherein said particles are partially dissolved by said acrylic Monomer.

37. The dental composition of claim 28 wherein said composition has a mass of at least 200 g, and said polymerizable acrylic compound is effectively maintained without polymerization for at least six months at 23° C.

38. The dental composition of claim 28 wherein said polymeric material has an unnotched Izod impact strength of at least 4.0 ft lbs/in as measured by Modified ASTM D256.

39. The dental composition of claim 38 wherein said acrylic Monomer comprises at least about 10 percent by weight of said polymerizable compounds and said polymeric material is adapted to withstand at least 1,000,000 flexes to break in the Flexural Fatigue of Denture Bases Test.

40. The dental composition of claim 38 wherein polymeric material is polymerized by heat curing and said polymerizable compounds further comprise less than 30 percent by weight of Volatile and said polymerizable compounds comprise at least 1 percent by weight of said composition.

41. The dental prosthesis of claim 1 wherein said polymerizable acrylic compound is within the scope of general formula:

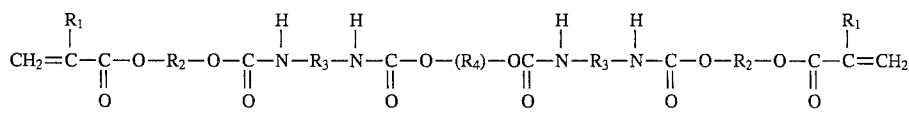

wherein each $R_1$ independently, is hydrogen, halogen, alkyl, or cyano moiety, each $R_2$ independently is alkylene, cycloalkylene, or arylene, each $R_3$ independently is alkylene, cycloalkylene, arylene, or heterocyclic, and $R_4$ is a polyester or polyether moiety.

42. The composition of claim 28 wherein said compound is within the scope of the general formula

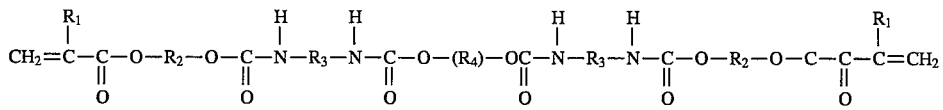

wherein each $R_1$ independently, is hydrogen, halogen, alkyl, substituted alkyl or cyano moiety, each $R_2$ independently is alkylene, cycloalkylene, or arylene, each $R_3$ independently is alkylene, cycloalkylene, arylene, or heterocyclic, and $R_4$ is a polyester or polyether moiety.

43. The dental prosthesis of claim 1 wherein said impact strength is at least 3.0 ft.lb/in as measured by Modified ASTM D256.

44. The dental prosthesis of claim 1 wherein said polymerizable acrylic compound has at least two acrylic moieties and is within the scope of the general formula:

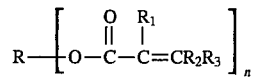

wherein R is an acrylic-free organic moiety which is at least 60 grams per molecule, $R_1$ is hydrogen, halogen, alkyl or cyano radical, $R_2$ and $R_3$ each independently is hydrogen or a halogen and n is an integer from 2 to 6.

45. The denture base of claim 17 wherein said polymerizable acrylic compound is within the scope of the general formula:

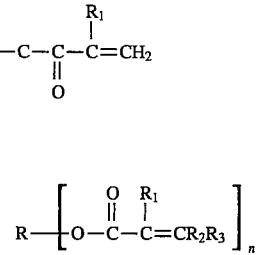

wherein R is an acrylic-free organic moiety which is at least 60 grams per molecule, $R_1$ is hydrogen, halogen, alkyl or cyano radical, $R_2$ and $R_3$ each independently is hydrogen or a halogen and n is an integer from 2 to 6.

46. The method of claim 24 wherein said polymerizable acrylic compound is within the scope of the general formula:

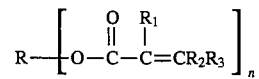

wherein R is an acrylic-free organic moiety which is at least 60 grams per molecule, $R_1$ is hydrogen, halogen, alkyl or cyano radical, $R_2$ and $R_3$ each independently is hydrogen or a halogen and n is an integer from 2 to 6.

* * * * *